United States Patent
Anderson-Cunanan et al.

(10) Patent No.: US 10,195,024 B2
(45) Date of Patent: Feb. 5, 2019

(54) PORCINE SMALL INTESTINE SUBMUCOSA LEAFLET MATERIAL

(71) Applicant: BOSTON SCIENTIFIC SCIMED, INC., Maple Grove, MN (US)

(72) Inventors: Crystal Marie Anderson-Cunanan, San Jose, CA (US); Katherine Cora Fazackerley, San Mateo, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 27 days.

(21) Appl. No.: 15/272,772

(22) Filed: Sep. 22, 2016

(65) Prior Publication Data
US 2017/0100238 A1 Apr. 13, 2017

Related U.S. Application Data

(60) Provisional application No. 62/238,285, filed on Oct. 7, 2015.

(51) Int. Cl.
*A61F 2/24* (2006.01)
*A61L 27/36* (2006.01)

(52) U.S. Cl.
CPC .......... *A61F 2/2415* (2013.01); *A61F 2/2418* (2013.01); *A61L 27/3629* (2013.01); *A61L 27/3687* (2013.01); *A61L 27/3691* (2013.01); *A61L 2430/20* (2013.01)

(58) Field of Classification Search
CPC ........ A61F 2/24; A61F 2/2412; A61F 2/2415; A61F 2/2418
See application file for complete search history.

(56) References Cited

U.S. PATENT DOCUMENTS

| | | |
|---|---|---|
| 2002/0094573 A1 | 7/2002 | Bell et al. |
| 2002/0103542 A1 | 8/2002 | Bilbo |
| 2003/0229394 A1 | 12/2003 | Ogle et al. |
| 2004/0078090 A1 | 4/2004 | Binette et al. |
| 2005/0143809 A1 | 6/2005 | Salahieh et al. |

(Continued)

FOREIGN PATENT DOCUMENTS

| | | |
|---|---|---|
| WO | 9825549 | 6/1998 |
| WO | 2017062198 | 4/2017 |

(Continued)

OTHER PUBLICATIONS

Cardinal, Kristen O. et al., "Tissue-Engineered Vascular Grafts as In Vitro Blood Vessel mimics for the Evaluation of Endothelialization of Intravascular Devices," Tissue Eng. 12, 3431-3438, 2006 (8 pages).

(Continued)

*Primary Examiner* — Jason-Dennis Stewart
(74) *Attorney, Agent, or Firm* — Pauly, DeVries Smith & Deffner LLC

(57) ABSTRACT

A prosthetic heart valve provided herein can include a porcine small intestine submucosa (P-SIS) tissue leaflet. The P-SIS tissue can include multiple stacked layers that are tensioned and cross-linked to form a material having a thickness of between 50 microns and 0.33 mm. In some cases, a prosthetic heart valve can include a plurality of leaflets secured together and retained within the expandable tubular member.

13 Claims, 3 Drawing Sheets

(56) References Cited

U.S. PATENT DOCUMENTS

| | | |
|---|---|---|
| 2005/0222661 A1* | 10/2005 | Case ................ A61F 2/2475 623/1.1 |
| 2006/0159722 A1 | 7/2006 | Braithwaite et al. |
| 2006/0253188 A1 | 11/2006 | Case et al. |
| 2007/0037283 A1 | 2/2007 | Patel et al. |
| 2007/0162103 A1 | 7/2007 | Case et al. |
| 2007/0254005 A1 | 11/2007 | Pathak et al. |
| 2009/0138078 A1* | 5/2009 | Paul, Jr. ............ A61F 2/2418 623/2.1 |
| 2009/0187241 A1 | 7/2009 | Melsheimer et al. |
| 2009/0216338 A1* | 8/2009 | Gingras ............ A61F 2/0063 623/23.72 |
| 2014/0277416 A1 | 9/2014 | Matheny et al. |
| 2016/0296323 A1 | 10/2016 | Wulfman et al. |
| 2017/0100237 A1 | 4/2017 | Anderson-Cunanan et al. |
| 2017/0128201 A1 | 5/2017 | Swanson et al. |

FOREIGN PATENT DOCUMENTS

| | | |
|---|---|---|
| WO | 2017062199 | 4/2017 |
| WO | 2017083183 | 5/2017 |

OTHER PUBLICATIONS

Gauvin, R. et al., "Dynamic Mechanical Stimulations Include Anisotropy and Improve the Tensile Properties of Engineered Tissues Produced Without Exogenous Scaffolding," Acta. Biomater. 7, 3294-3301, 2011 (8 pages).

Kalejs, et al., "St. Jude Epic Heart Valve Bioprostheses Versus Native Human and Porcine Aortic Valves—Comparison of Mechanical Properties," Interactive Cardiovascular and Thoracic Surgery 8 (2009) 553-557.

Kelm, J. M. et al., "Scaffold-Free Cell Delivery for Use in Regenerative Medicine," Adv. Drug Deliv. Rev. 62, 753-764, 2010 (12 pages).

L'Heureux, N. et al., "A Completely Biological Tissue-Engineered Human Blood Vessel," FASEB J. 12, 47-56, 1998 (10 pages).

Milleret, Vincent et al., "Tuning Electrospinning Parameters for Production of 3D-Fiber-Fleeces with Increased Porosity for Soft Tissue Engineering Applications," Eur. Cell. Mater. 21, 286-303, 2011 (18 pages).

Schellenberg, Anne et al., "3D Non-Woven Polyvinylidene Fluoride Scaffolds: Fibre Cross Section and Texturizing Patterns Have Impact on Growth of Mesenchymal Stromal Cells," Plos One 9(4) e94353, 2014 (9 pages).

Billiar, Kristen L. et al., "Biaxial Mechanical Properties of the Native and glutaraldehyde-Treated Aortic Valve Cusp: Part II—A Structural Constitutive Model," Journal of Biomechanical Engineering (2000) vol. 122, pp. 327-335.

"International Search Report and Written Opinion," for PCT Application PCT/US2016/053680 dated Dec. 16, 2016 (12 pages).

"International Search Report and Written Opinion," for PCT Application PCT/US2016/053682 dated Jan. 3, 2017 (13 pages).

"International Search Report and Written Opinion," for PCT Application PCT/US2016/060449 dated Feb. 24, 2017 (12 pages).

Kelm, J. M. et al., "A Novel Concept for Scaffold-Free Vessel Tissue Engineering: Self-Assembly of Microtissue Building Blocks," Journal of Biotechnology, 148 (2010): pp. 46-55.

"Non-Final Office Action," for U.S. Appl. No. 15/272,747 dated Oct. 19, 2017 (17 pages).

"Response to Non-Final Office Action," for U.S. Appl. No. 15/272,747, dated Oct. 19, 2017 and filed with the USPTO Dec. 20, 2017 (9 pages).

"Non-Final Office Action," for U.S. Appl. No. 15/340,242 dated Apr. 10, 2018 (22 pages).

\* cited by examiner

PORCINE SMALL INTESTINE SUBMUCOSA LEAFLET MATERIAL

This application claims the benefit of U.S. Provisional Application No. 62/238,285, filed Oct. 7, 2015, the contents of which are herein incorporated by reference.

FIELD

This document provides leaflets made out of porcine small intestine submucosa tissue.

BACKGROUND

Heart valve surgery can be used to repair or replace diseased heart valves. For example, heart valve replacement may be indicated when there is a narrowing of the native heart valve, commonly referred to as stenosis, or when the native valve leaks or regurgitates. The repair or replacement of diseased heart valves can include, for example, the introduction of a prosthetic heart valve that includes biological tissue heterologous to the patient (e.g., a heterograft or xenograft). A common biological tissue used to make prosthetic heart valves is pericardial tissue, typically bovine or porcine.

SUMMARY

Prosthetic heart valves provided herein use porcine small intestine submucosa tissue as the leaflet material. In the gastrointestinal tract, the submucosa is the layer of dense irregular connective tissue or loose connective tissue that supports the mucosa, as well as joins the mucosa to the bulk of overlying smooth muscle (fibers running circularly within layer of longitudinal muscle). Prosthetic heart valves provided herein can include porcine small intestine submucosa (hereinafter "P-SIS") tissue that has been lyophilized, rehydrated, and cross-linked with an aldehyde. In some cases, the P-SIS can be cross-linked with an aldehyde while it is under tension.

In Example 1, a prosthetic heart valve can include a plurality of leaflets secured together and retained within the expandable tubular member, where each leaflet includes cross-linked porcine small intestine submucosa tissue.

In Example 2, a prosthetic heart valve of Example 1 where the small intestine submucosa tissue includes multiple layers of P-SIS tissue.

In Example 3, a prosthetic heart valve of Example 1 or Example 2, wherein the porcine small intestine submucosa tissue has a total thickness of between 50 microns and 0.33 mm.

In Example 4, a prosthetic heart valve of one of Examples 1-3, where the porcine small intestine submucosa tissue was lyophilized and rehydrated.

In Example 5, a prosthetic heart valve of one of Examples 1-4, where the porcine small intestine submucosa tissue has a moisture content of between 75% and 85%.

In Example 6, a prosthetic heart valve of one of Examples 1-5, where the porcine small intestine submucosa tissue has an ultimate tensile strength of between 2 MPa and 10 MPa.

In Example 7, a prosthetic heart valve of one of Examples 1-6, where the porcine small intestine submucosa tissue has a modulus of between 16.5 and 42.5.

In Example 8, a prosthetic heart valve of one of Examples 1-7, where the porcine small intestine submucosa tissue has a percent elongation at 1 MPa of between 5% and 10%.

In Example 9, a prosthetic heart valve of one of Examples 1-8, where the porcine small intestine submucosa tissue has an elongation to break at between 25% and 47%.

In Example 10, a prosthetic heart valve of one of Examples 1-9, where the tissue is bi-axially oriented.

In Example 11, a prosthetic heart valve of one of Examples 1-10, where tissue is cross-linked by submerging the porcine small intestine submucosa tissue in a solution of between 0.1 and 1.5 wt % glutaraldehyde for at least 10 minutes.

In Example 12, a prosthetic heart valve of one of Examples 1-10, where the tissue is cross-linked by submerging the porcine small intestine submucosa tissue in a solution of between 0.5 and 1.0 wt % glutaraldehyde for at least 30 minutes.

In Example 13, a prosthetic heart valve of one of Examples 1-10, where the tissue is cross-linked by submerging the porcine small intestine submucosa tissue in a solution of between 0.5 and 0.7 wt % glutaraldehyde for at least 2 hours.

In Example 14, a prosthetic heart valve of one of Examples 1-13, where the leaflets consist of the cross-linked porcine small intestine submucosa tissue.

In Example 15, a method of forming a porcine small intestine submucosa leaflet includes: (a) obtaining porcine small intestine submucosa; (b) cutting and stacking multiple layers of the porcine small intestine submucosa into a substantially planar patch of porcine small intestine submucosa tissue having a thickness of at least 50 microns; (c) applying tension to the patch of porcine small intestine submucosa tissue; (d) contacting the porcine small intestine submucosa tissue with a chemical cross-linker for at least 10 minutes to cross-link the patch; and (e) cutting out a leaflet from the patch, the leaflet comprising a body portion and two sleeve portions.

In Example 16, the method of Example 15 where the chemical cross-linker is glutaraldehyde.

In Example 17, the method of Example 16 where the porcine small intestine submucosa tissue is submerged in a solution comprises between 0.1 and 1.5 wt % glutaradehyde to cross-link the porcine small intestine submucosa.

In Example 18, the method of Example 16 where the tissue is cross-linked by submerging the porcine small intestine submucosa tissue in a solution of between 0.5 and 1.0 wt % glutaraldehyde for at least 30 minutes.

In Example 19, the method of Example 16 where the tissue is cross-linked by submerging the porcine small intestine submucosa tissue in a solution of between 0.5 and 0.7 wt % glutaraldehyde for at least 2 hours.

In Example 20, the method of one of Examples 15-19 where the porcine small intestine submucosa is obtained in a lyophilized state and is further rehydrated prior to stacking the cutting the multiple layers of tissue.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
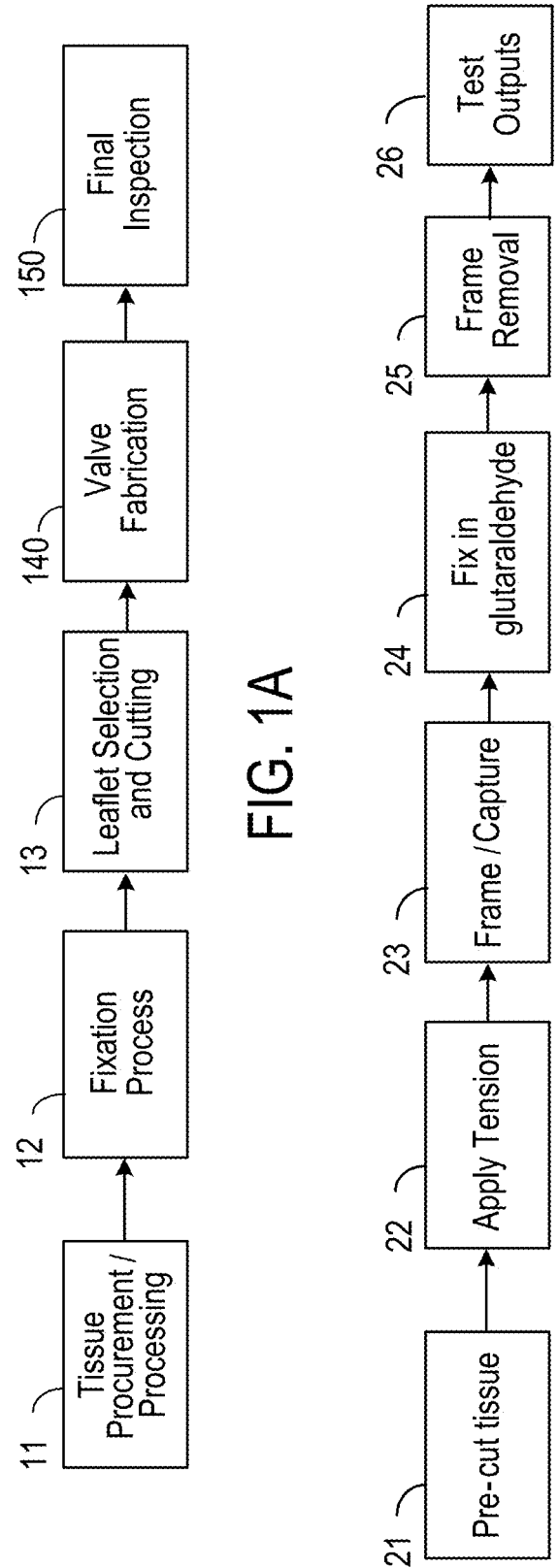
FIG. 1A is flow chart depicting an exemplary method for producing a heart valve using porcine small intestine submucosa tissue.
FIG. 1B is a flow chart depicting a method of treating porcine small intestine submucosa tissue according to some embodiments of the methods provided herein.

Prosthetic heart valves provided herein include lyophilized and aldehyde cross-linked P-SIS tissue leaflets. Prosthetic heart valves have typically used bovine or porcine pericardium tissue leaflets, but these tissues can be too thick. P-SIS tissue that has been lyophilized, rehydrated, and cross-linked with an aldehyde, such as glutaraldehyde, can provide superior mechanical properties and thinner wall thicknesses than bovine or porcine pericardium tissue leaflets. In some cases, sheet thickness can be controlled by using one or more layers of P-SIS tissue. For example, a layer of P-SIS tissue can have a thickness of between 15 and 20 microns. Multiple layers of P-SIS, however, can be stacked to have a thickness of between 50 microns and 0.33 mm. In some cases, the leaflets have a moisture content of between 75% and 85% (e.g., about 79% on average), have an ultimate tensile strength of between 4.6 MPa and 7.15 MPa (e.g., about 5.77 MPa on average), have a modulus of between 16.5 and 42.5 (e.g., about 27 on average), have a percent elongation at 1 MPa of between 5.5% and 8.4% (e.g., about 6.7% on average), and an elongation to break at between 25% and 47% (e.g., about 32% on average). In some cases, the P-SIS tissue can be biaxially tensioned while being cross-linked to provide a leaflet having thickness of less than 0.33 mm. In some cases, biaxially tensioned and fixed P-SIS tissue leaflets provided herein can have a maximum thickness of less than 0.2 mm. In some cases, biaxially tensioned and fixed P-SIS tissue leaflets provided herein can have a maximum thickness of between 50 microns and 0.33 mm based on multiple layers of P-SIS tissue. In some cases, the P-SIS tissue is bi-axially tensioned by applying a stress load of at least 0.1 N to stretch the porcine small intestine submucosa tissue along two intersecting axes. In some cases, the P-SIS tissue is bi-axially tensioned by applying a stress load of between 0.1 N and 2 N to stretch the porcine small intestine submucosa tissue along two intersecting axes. In some cases, the P-SIS tissue is bi-axially tensioned by applying a stress load of between 0.5 N and 1 N to stretch the porcine small intestine submucosa tissue along two intersecting axes. The stress load in one direction can be different than in the other axis to create controlled anisotropy in the material. The P-SIS tissue can be chemically cross-linked while under tension to prevent recoil of the porcine small intestine submucosa tissue after the tension is released. The biaxially oriented and fixed P-SIS tissue provides a suitable material properties for valve leaflets while providing a superior profile due to its thinner nature. Furthermore, methods, devices, and systems provided herein can provide reliable and consistent mechanical properties for P-SIS tissue leaflets used in prosthetic heart valves.

In some cases, leaflets provided herein have a moisture content of between 75% and 85% (e.g., about 79% on average). The moisture can impart appropriate mechanical properties. In some cases, a leaflet provided herein can have a moisture of between 60% and 95%, between 65% and 90%, between 70% and 88%, between 75% and 85%, between 77%, and 82%, or between 78% and 80%. Moisture can be measured using any suitable technique. In some cases, the moisture content can be measured by placing a leaflet in an evacuated chamber at a temperature greater than 100° C. for at least 1 hour to measure dry the leaflet, and calculate the weight of the moisture originally in the leaflet by comparing the original weight to the dried leaflet weight.

In some cases, leaflets provided herein have an ultimate tensile strength of between 4.6 MPa and 7.15 MPa (e.g., about 5.77 MPa on average). The ultimate tensile strength of the leaflet impacts the suitability of the material for use as a leaflet. In some cases, leaflets provided herein can have a thinner profile while having a desirable ultimate tensile strength. The ultimate tensile strength can be measured using any suitable technique, including ASTM D412. In some cases, a leaflet provided herein can have a ultimate tensile strength between 4.0 MPa and 8.0 MPa between 4.3 MPa and 7.5 MPa, between 4.6 MPa and 7.15 MPa, between 5.0 MPa and 6.5 MPa, or between 5.5 MPa and 6.0 MPa.

In some cases, leaflets provided herein have a modulus of between 16.5 and 42.5 (e.g., about 27 on average). The modulus of the leaflet impacts the suitability of the material for use as a leaflet. In some cases, leaflets provided herein can have a thinner profile while having a desirable modulus. The modulus can be measured using any suitable technique, including ASTM D1415. In some cases, a leaflet provided herein can have a modulus between 10 and 50, between 15 and 45, between 16.5 and 42.5, between 20 and 35, or between 25 and 30.

In some cases, leaflets provided herein have a percent elongation at 1 MPa of between 5.5% and 8.4% (e.g., about 6.7% on average). The percent elongation at 1 MPa of the leaflet impacts the suitability of the material for use as a leaflet. In some cases, leaflets provided herein can have a thinner profile while having a desirable percent elongation at 1 MPa. The percent elongation at 1 MPa can be measured using any suitable technique, including ASTM D412. In some cases, a leaflet provided herein can have a percent elongation at 1 MPa between 4% and 10%, between 5% and 9%, between 5.5% and 8.4%, between 6% and 7.5%, or between 6.5% and 7.0%.

In some cases, leaflets provided herein have an elongation to break at between 25% and 47% (e.g., about 32% on average). The elongation to break of the leaflet impacts the suitability of the material for use as a leaflet. In some cases, leaflets provided herein can have a thinner profile while having a desirable elongation to break. The elongation to break can be measured using any suitable technique, including ASTM D412. In some cases, a leaflet provided herein can have an elongation to break between 20% and 60%, between 25% and 47%, or between 30% and 35%.

FIG. 1A is a flow chart depicting the overall process of incorporating porcine small intestine submucosa tissue into a prosthetic heart valve. The first step 11 is to procure a porcine small intestine submucosa for use in a prosthetic heart valve. Initial P-SIS as to be harvested, then cleaned, isolated, and processed to produce sheets. In some cases, the P-SIS tissue can be provided in a lyophilized state. For example, lyophilized P-SIS in a non-cross-linked form is sometimes commercially available as a wound healing product. In some cases, a lyophilized P-SIS tissue is obtained and by rehydrated by submersion in a saline solution. In some cases, the P-SIS tissue is never lyophilized.

Figure 2:
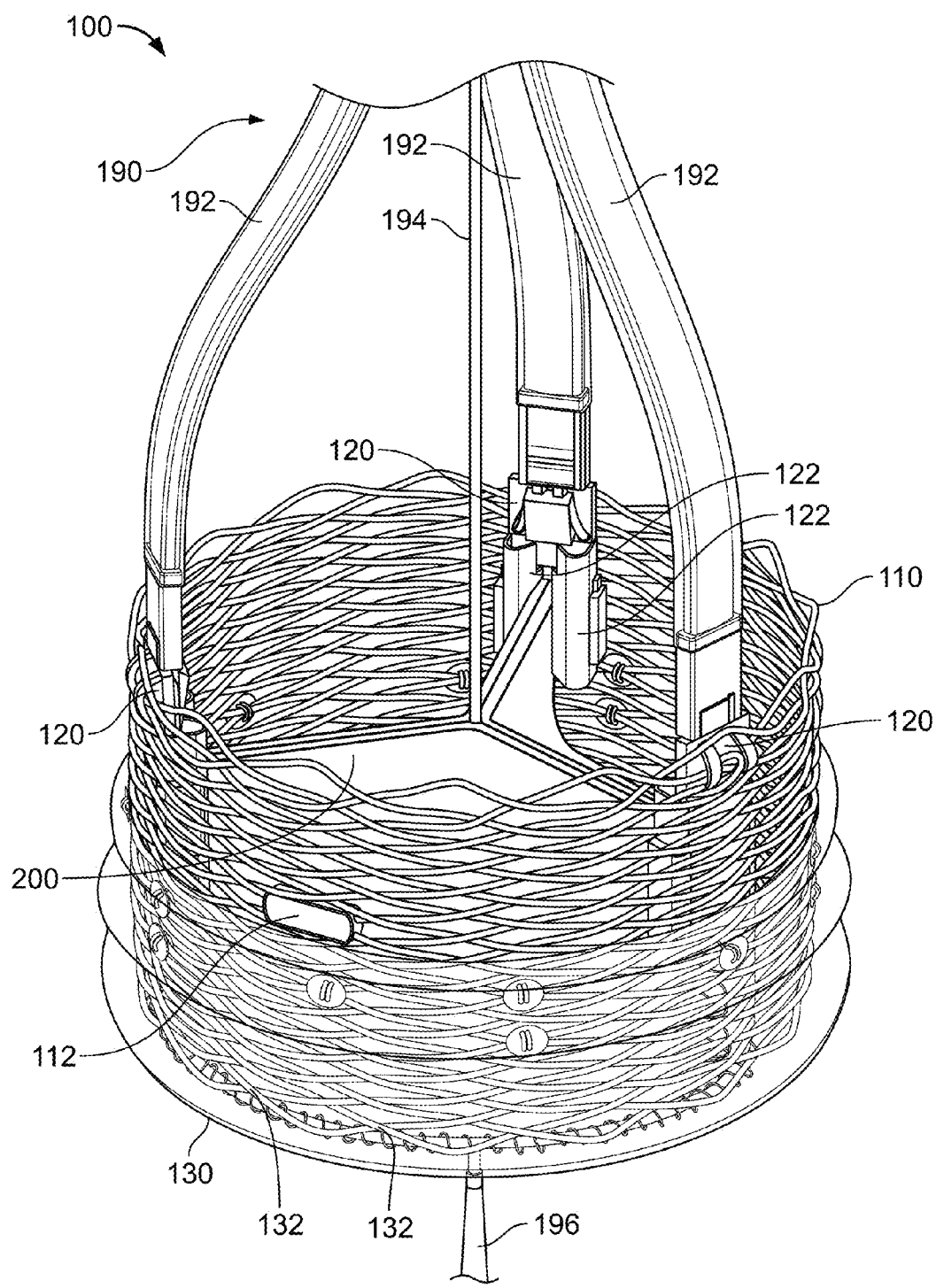
FIG. 2 is an exemplary prosthetic heart valve.

The P-SIS tissue can be fixed in step 12, which is described below. In some cases, multiple layers of P-SIS tissue are stacked and fixed together in step 12. In step 13, leaflets having a predetermined shape are cut from the fixed P-SIS tissue, and suitable leaflets selected for use in a prosthetic heart valve. In step 14, a prosthetic heart valve is fabricated using one or more of the cut leaflets. For example, FIG. 2 depicts an exemplary prosthetic heart valve. In some cases, three leaflets including the biaxially oriented, and fixed P-SIS tissue can be stitched to a frame and/or to each other to form a prosthetic heart valve. In step 15, prosthetic heart valves can be inspected and/or tested to ensure that they meet specifications. In some cases, a prosthetic heart valve can be sterilized before or after inspection.

An exemplary processes of fixing P-SIS tissue 12 is further shown in the flow chart of FIG. 1B. Processes provided herein for P-SIS tissue modification can use one or more of the steps depicted in FIG. 1B. In step 21, layers of P-SIS tissue are cut to simplify the tissue modification processes provided in steps 22-26. In some cases, multiple layers of P-SIS tissue are tacked and cut into a patch. The patch of P-SIS tissue can be substantially rectangular. In some cases, the patch of P-SIS tissue can be cut such that it can be laid in a substantially flat configuration. In some cases, the patch of P-SIS tissue can be cut such that thickness variations are minimized. Step 21 can be performed by hand with the aid of a template approximating the shape of the biological tissue. In some cases, step 21 can be automated using opposite male and female mold members and a control system to cut the biological tissue along predetermined lines. Although the P-SIS tissue can be cut in step 21 to minimize variations in mechanical properties of the P-SIS tissue in the patch, natural variations are expected, thus the devices, systems, and methods provided herein can further tension and fix the P-SIS tissue to produce reliable and consistent mechanical properties in the porcine small intestine submucosa tissue. In some cases, the stacked layers of P-SIS tissue can have an initial thickness of about 0.14 mm to about 0.24 mm.

Figure 3:
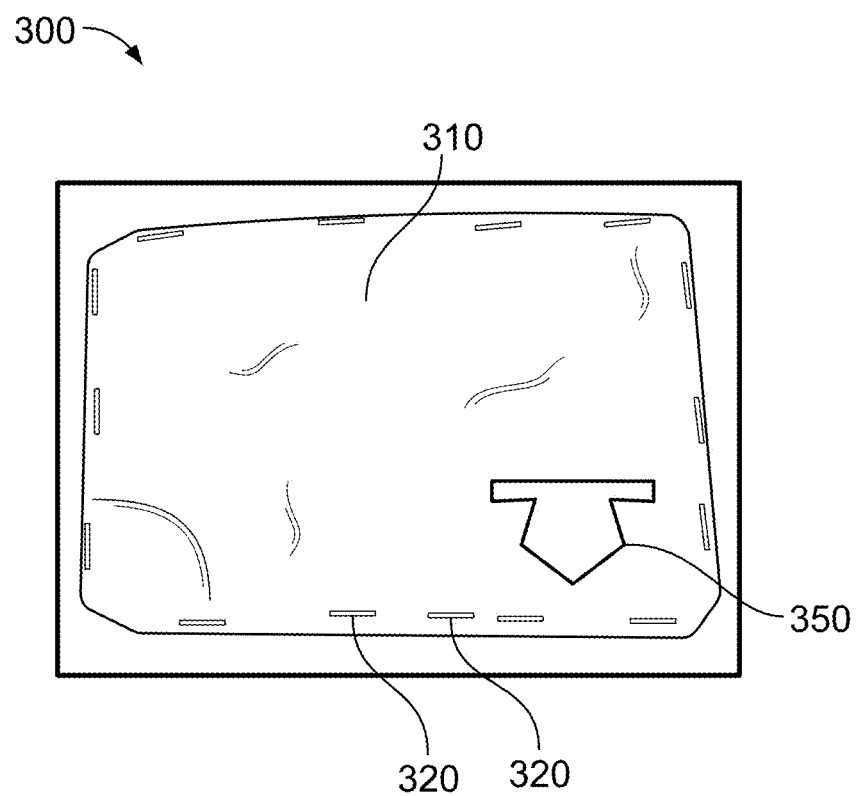
FIG. 3 depicts a frame for securing biaxially tensioned porcine small intestine submucosa tissue for treatment and cutting of leaflets.

In step 22, the P-SIS tissue can be optionally tensioned. For example, a plurality of grippers can be arranged around a patch of P-SIS tissue placed over a frame and stretched to tension the patch of P-SIS tissue. As discussed above, the patch of P-SIS tissue can include multiple layers of P-SIS tissue. In step 23, the tensioned patch of P-SIS tissue is captured on a frame, such as shown in FIG. 3, to retain the tensioning for further processing. For example, as shown in FIG. 3, tensioned patch 310 can be secured on the frame by a plurality of staple 320 to create a tissue-frame assembly 300. In step 24, the tensioned patch is chemically cross-linked to fix the P-SIS tissue. As shown, step 24 can use a gluteraldehyde. In some cases, tissue-frame assembly 300 can be placed in a solution including 0.6 wt % gluteraldehyde for at least 10 minutes to chemically cross-link the P-SIS tissue. In some cases, other chemical cross-linkers, such as carbodiimide, can be used to chemically cross-link the porcine small intestine submucosa tissue on the frame. Cross-linked P-SIS tissue exhibits superior resistance to protease degratdation compared to non-cross-linked P-SIS tissues, thus making cross-linked P-SIS material suitable for use as a heart valve leaflet material.

In step 25, oriented, and fixed P-SIS tissue can be separated from the frame. In some cases, the oriented and fixed P-SIS tissue can be cut from the fixed and tensioned P-SIS tissue while the P-SIS tissue is still secured to the frame. For example, a leaflet 350 can be cut out of patch 310, as shown in FIG. 3. In some cases, the P-SIS tissue can be removed from the frame and subsequently cut. In step 26, the P-SIS tissue is tested to determine if it meets specifications.

FIG. 2 illustrates an exemplary prosthetic heart valve 100 provided herein, which can use leaflets 200 including tensioned and fixed P-SIS tissue provided herein. FIG. 2 is a perspective views of prosthetic heart valve 100 connected to a deployment device 190. As shown, prosthetic heart valve 100 includes an expandable member 110 (e.g., a braided stent), three bi-axially oriented and fixed P-SIS leaflets 200, three anchor elements 120 that secure sleeve portions 216 of leaflets 200 to expandable member 110, and a tubular seal 130 secured around a blood inflow end of prosthetic heart valve 100. To facilitate better understanding, FIG. 2 does not show components that are located underneath tubular seal 130. Anchor elements 120 can include post leg compression elements 122 and clamping support structures 126 adapted to provide support along opposite sides of the sleeve portions 216. Expandable member 110 shown in FIG. 2 is a braided stent (which can also be described as a braided anchor element), which is adapted to transition between a restricted state having a smaller diameter and an expanded state having a larger diameter. Expandable member 110 can be self-expanding, mechanically expanded, or a combination thereof. In some cases, one or more radiopaque markers can be secured to prosthetic heart valves provided herein. As shown, expandable member 110 includes a radiopaque marker 112. Any suitable radiopaque material (such as platinum, palladium, gold, tantalum, or alloys thereof) can be used as the radiopaque material in radiopaque marker 112. One or more radiopaque markers can be used with an imaging system to help a physician ensure that a valve is set in an appropriate location. In some cases, prosthetic heart valves provided herein include at least three radiopaque markers. Expandable member 110 can have any suitable structure, arrangement, or material. In some cases, expandable member 110 can include a braided wire stent. For example, U.S. Publication Number 2005/0143809, titled, "Methods and Apparatus for Endovascularly Replacing a Heart Valve," and filed on Nov. 5, 2004, which is herein incorporated by reference for its disclosure of possible structures and materials for a braided wire stent, discloses a braided wire stent. In some cases, expandable member 110 includes a shape memory material (e.g., a nickel-titanium alloy or a cobalt-chromium alloy).

In some cases, as shown, prosthetic heart valve 100 includes three P-SIS leaflets 200. In some cases, prosthetic heart valves provided herein can have any suitable number of P-SIS leaflets, such as two, three, four, five, or more leaflets. In some cases, P-SIS leaflets 200 are secured to one another. In some cases, P-SIS leaflets 200 can be secured to one another by a suture (not shown) or a plurality of sutures. P-SIS leaflets 200 can be sutured alongside edges of a body portion of each leaflet. In some cases, prosthetic heart valves provided herein can include a single line of sutures, which can be adapted to minimize leaks, minimize the width of a seam, and/or minimize the profile of a replacement heart valve during a percutaneous insertion. In some cases, prosthetic heart valves provided herein can include multiple lines of sutures.

Referring back to FIG. 1B, step 22, a patch of P-SIS tissue can be tensioned according to methods, devices, or systems provided herein. In some cases, a patch of biological tissue can be tensioned by securing the edges of the patch to a plurality of grippers and applying an equal amount of actuating force to each of the grippers. In some cases, a patch of biological tissue provided herein can be along a single axis for a uniaxial orientation. In some cases, a patch of biological tissue provided herein can be stretched along two axes to for a biaxial orientation. In some cases, an amount of force supplied along the two intersecting axes is equal. In some cases, an amount of force supplied along the two intersecting axes is different. In some cases, the axes are perpendicular. In some cases, force is supplied along each axes such that each gripper supplies an equal amount of stretching force to the biological tissue.

A number of embodiments of the invention have been described. Nevertheless, it will be understood that various modifications may be made without departing from the spirit and scope of the invention. Accordingly, other embodiments are within the scope of the following claims.

What is claimed is:

1. A prosthetic heart valve comprising a plurality of leaflets secured together and retained within an expandable tubular member, each leaflet comprising a chemically cross-linked porcine small intestine submucosa tissue;
wherein the chemically cross-linked porcine small intestine submucosa tissue is chemically cross-linked while under tension.

2. The prosthetic heart valve of claim 1, wherein the porcine small intestine submucosa tissue includes multiple layers of P-SIS tissue.

3. The prosthetic heart valve of claim 2, wherein the porcine small intestine submucosa tissue has a total thickness of between 50 microns and 0.33 mm.

4. The prosthetic heart valve of claim 1, wherein the porcine small intestine submucosa tissue was lyophilized and rehydrated.

5. The prosthetic heart valve of claim 1, wherein the porcine small intestine submucosa tissue has a moisture content of between 75% and 85%.

6. The prosthetic heart valve of claim 1, wherein the porcine small intestine submucosa tissue has an ultimate tensile strength of between 2 MPa and 10 MPa.

7. The prosthetic heart valve of claim 1, wherein the porcine small intestine submucosa tissue has a modulus of between 16.5 and 42.5.

8. The prosthetic heart valve of claim 1, wherein the porcine small intestine submucosa tissue has a percent elongation at 1 MPa of between 5% and 10%.

9. The prosthetic heart valve of claim 1, wherein the porcine small intestine submucosa tissue has an elongation to break at between 25% and 47%.

10. The prosthetic heart valve of claim 1, wherein the chemically cross-linked porcine small intestine submucosa tissue is bi-axially oriented.

11. The prosthetic heart valve of claim 1, wherein the tissue is cross-linked by submerging the porcine small intestine submucosa tissue in a solution of between 0.1 and 1.5 wt % glutaraldehyde for at least 10 minutes.

12. The prosthetic heart valve of claim 11, wherein the tissue is cross-linked by submerging the porcine small intestine submucosa tissue in a solution of between 0.5 and 1.0 wt % glutaraldehyde for at least 30 minutes.

13. The prosthetic heart valve of claim 11, wherein the tissue is cross-linked by submerging the porcine small intestine submucosa tissue in a solution of between 0.5 and 0.7 wt % glutaraldehyde for at least 2 hours.

* * * * *